United States Patent
Bora et al.

(10) Patent No.: US 10,227,303 B2
(45) Date of Patent: Mar. 12, 2019

(54) PROCESS FOR THE PREPARATION OF HALOSUBSTITUTED TRIFLUOROMETHYLPYRIDINES

(71) Applicant: SRF LIMITED, Gurgaon (IN)

(72) Inventors: Pushkar Singh Bora, Gurgaon (IN); Prabhu Balaji, Gurgaon (IN); Chandresh Soni, Gurgaon (IN); Kapil Kumar, Gurgaon (IN); Rajdeep Anand, Gurgaon (IN)

(73) Assignee: SRF Limited, Gurgaon (IN)

( * ) Notice: Subject to any disclaimer, the term of this patent is extended or adjusted under 35 U.S.C. 154(b) by 0 days.

(21) Appl. No.: 15/571,517

(22) PCT Filed: May 5, 2016

(86) PCT No.: PCT/IN2016/050126
§ 371 (c)(1),
(2) Date: Nov. 3, 2017

(87) PCT Pub. No.: WO2016/178248
PCT Pub. Date: Nov. 10, 2016

(65) Prior Publication Data
US 2018/0141908 A1    May 24, 2018

(30) Foreign Application Priority Data
May 5, 2015   (IN) ............................ 1250/DEL/2015

(51) Int. Cl.
C07D 213/61    (2006.01)
(52) U.S. Cl.
CPC .................. C07D 213/61 (2013.01)

(58) Field of Classification Search
None
See application file for complete search history.

(56) References Cited

U.S. PATENT DOCUMENTS

| | | |
|---|---|---|
| 4,266,064 A | 5/1981 | Nishiyama et al. |
| 4,563,529 A | 1/1986 | Nishiyama et al. |

FOREIGN PATENT DOCUMENTS

| | | | |
|---|---|---|---|
| CN | 101081831 A | 12/2007 | |
| DE | 19536811 A1 * | 4/1997 | ............. A01N 55/04 |
| WO | 2015151116 A2 | 10/2015 | |

OTHER PUBLICATIONS

Rheinhemier et al, Chemical Abstracts 126:317495 (Abstract of DE 19536811), (Year: 1997).*
Patent Cooperation Treaty (PCT), International Search Report and Written Opinion for Application PCT/IN2016/050126, filed May 5, 2015, dated Aug. 22, 2016, International Searching Authority, EP.

* cited by examiner

*Primary Examiner* — Zinna Northington Davis
(74) *Attorney, Agent, or Firm* — Dinsmore & Shohl LLP

(57) ABSTRACT

The present invention provides a process for the preparation of halosubstituted-6-trifluoromethyl pyridine of Formula I Formula I

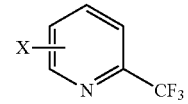

wherein X is a halogen.

7 Claims, No Drawings

PROCESS FOR THE PREPARATION OF HALOSUBSTITUTED TRIFLUOROMETHYLPYRIDINES

CROSS REFERENCE TO RELATED APPLICATIONS

This application is a 35 U.S.C. 371 national stage filing and claims priority to International Application No. PCT/IN2016/050126 filed on May 5, 2016, entitled "PROCESS FOR THE PREPARATION OF HALO SUBSTITUTED TRIFLUOROMETHYLPYRIDINES," which claims the benefit of Indian Patent Application No. 1250/DEL/2015 filed on May 5, 2015, each of which is incorporated herein in its entirety by reference.

FIELD OF THE INVENTION

The present invention provides a process for the preparation of halosubstituted 6-trifluoromethylpyridine of Formula I.

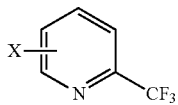

Formula I wherein X is a halogen

BACKGROUND OF THE INVENTION

The substituted pyridines, especially, halo substituted trifluoromethylpyridines are key intermediates in the synthesis of pesticides, insecticides, herbicides and the like. It is also widely used in organic synthesis, pharmaceuticals and dye.

The U.S. Pat. No. 4,563,529 provides a process for producing trifluoromethylpyridine, by reacting a pyridine derivative selected from α-picoline, γ-picoline and a lutidine with chlorine and anhydrous hydrogen fluoride under inert gas atmosphere at a temperature of 300° C. to 600° C. in vapour phase in the presence of a diluent and a catalyst comprising a fluoride of a metallic element. The process produces 6-chloro-2-trifluoromethyl pyridine with a low yield ranging from 37.4% to 48.3% by gas chromatography.

The present inventors observed that prior art generates low yield of 2-chloro-6-trifluoromethylpyridine with low purity along with the formation of excess bi-products. The present invention provides a process for the preparation of substituted pyridines, especially, halo substituted trifluoromethylpyridines which is simple, easy to perform and industrially doable. The present invention provides halo substituted trifluoromethylpyridines with high yield. Additionally, the present invention has advantage of advanced catalyst life.

OBJECTIVE OF THE INVENTION

The main object of the present invention is to provide a process for the preparation of substituted pyridine of Formula I

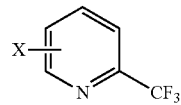

Formula I wherein X is a halogen.

SUMMARY OF THE INVENTION

The present invention provides a process for the preparation of Formula I, comprising;
a) reacting compound of Formula II with anhydrous hydrogen fluoride in the presence of a fluorination catalyst to obtain compound of Formula I, and

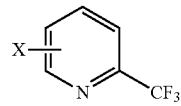

Formula I

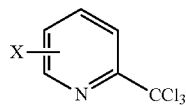

Formula II wherein X is a halogen
b) isolating the compound of Formula I from the step a) reaction mixture, wherein the step a) takes place in a vapour phase in the absence of inert gas.

The present invention also provides a process for the preparation of halo substituted trifluoromethylpyridines of Formula I, comprising;
a) reacting compound of Formula II having purity greater than 98.0% with anhydrous hydrogen fluoride in the presence of a fluorination catalyst to obtain compound of Formula I, and
b) isolating the compound of Formula I from the step a) reaction mixture, wherein the step a) takes place in a vapour phase in the absence of inert gas.

DETAILED DESCRIPTION OF THE INVENTION

The present invention provides a process for the preparation of Formula I, comprising;
a) reacting compound of Formula II with anhydrous hydrogen fluoride in the presence of a fluorination catalyst to obtain compound of Formula I, and

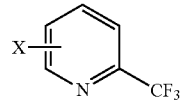

Formula I

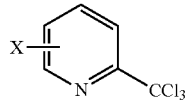

Formula II wherein X is a halogen b) isolating the compound of Formula I from the step a) reaction mixture, wherein the step a) takes place in a vapour phase in the absence of inert gas.

The present invention also provides a process for the preparation of halo substituted trifluoromethylpyridines of Formula I, comprising;
  a) reacting compound of Formula II having purity greater than 98.0% with anhydrous hydrogen fluoride in the presence of a fluorination catalyst to obtain compound of Formula I, and
  b) isolating the compound of Formula I from the step a) reaction mixture, wherein the step a) takes place in a vapour phase in the absence of inert gas.

The compound of Formula II may be obtained commercially or can be prepared by any of the methods known in the art.

The fluorination catalyst is selected from oxides or fluorides of one or more of chromium, manganese, iron, cobalt, aluminium or nickel. The catalyst may be used either unsupported or supported, supported materials may be selected from aluminium fluoride, alumina, silica-alumina. The invention may be carried out in the presence of pure oxygen.

The process of the present invention is solvent-free. The process of the present invention is continuous.

The step a) is carried out in the absence of any inert gas. The inert gas can be nitrogen, helium and argon.

The process of the present invention is carried out at a temperature in the range of from about 300° C. to 400° C., for example, from about 330° C. to 380° C.

In usual, gaseous materials containing the fluorinated products as main component, the unreacted anhydrous hydrogen fluoride, the intermediates, hydrogen chloride as a by-product are discharged from the reaction tube. The trifluoromethylpyridines are obtained as a liquid mixture through a desired cooling and condensing device.

The unwanted intermediates and by-products may be converted to halo substituted trifluoromethylpyridines by re-cyclization. Further, the halo substituted trifluoromethylpyridines may be isolated from the reaction mixture by the methods known in the art, for example, filtration, decantation, layer separation, precipitation, distillation and evaporation or a mixture thereof.

The halo substituted trifluoromethylpyridines prepared by virtue of the process of present invention is pure to greater than 97.0%, preferably greater than 97.5% by GC.

The term 'about' refers to a variation of 10% on the higher and lower side of specified parameter.

While the present invention has been described in terms of its specific embodiments, certain modifications and equivalents will be apparent to those skilled in the art and are intended to be included within the scope of the present invention.

The following examples are given by way of illustration and therefore should not be construed to limit the scope of the present invention.

EXAMPLES

Example 1: Preparation of 2-chloro-6-trifluoromethylpyridine 2-chloro-6-trichloromethyl pyridine (700 g, 3.03 moles, feed rate 1.24 g/min) and anhydrous hydrogen fluoride (936 g, 46.8 moles, feed rate 1.66 g/min) in the absence of inert gas were fed in to a tubular reactor packed with pre activated chromia-alumina catalyst (210 g) at 330° C. Reactor outlet material was collected in ice-cooled water and it was extracted with dichloromethane. Dichloromethane layer was washed with 10% potassium hydroxide solution and the organic layer was separated out and it was concentrated to get 490.0 g of crude 2-chloro-6-trifluoromethypyridine. The purity of crude product was 95.03% by GC analysis. Reaction yield on the basis of crude product obtained is 89%. The crude product was purified by fractional distillation to obtain 2-chloro-6-trifluoromethypyridine with the
Purity (%): 98.0
Yield (%): 80.0

What is claimed is:
1. A process for preparation of 2-chloro-6-trifluoromethylpyridine comprising;
  a) reacting a reaction mixture consisting of 2-chloro-6-trichloromethyl pyridine with anhydrous hydrogen fluoride in the presence of a chromia-alumina catalyst and
  b) isolating 2-chloro-6-trifluoromethylpyridine from the step a) reaction mixture, wherein the step a) takes place in a vapour phase in the absence of inert gas.

2. The process as claimed in claim 1, wherein the catalyst used is either unsupported or supported.

3. The process as claimed in claim 1, wherein step a) or step b) or both are carried out in the presence of pure oxygen.

4. The process as claimed in claim 1, wherein the process is continuous.

5. The process as claimed in claim 1, wherein the inert gas is nitrogen, helium and argon.

6. The process as claimed in claim 1, wherein the process is carried out at a temperature of 300° C. to 400° C.

7. The process as claimed in claim 1, wherein the compound of Formula I is isolated from the reaction mixture by filtration, decantation, layer separation, precipitation, distillation and evaporation or a mixture thereof.

* * * * *